(12) United States Patent
Kwolek et al.

(10) Patent No.: US 11,123,494 B2
(45) Date of Patent: *Sep. 21, 2021

(54) EXOSTRUCTURE TO ASSIST IN ACCURATE SYRINGE INJECTION

(71) Applicant: KB Medical, LLC, Las Vegas, NV (US)

(72) Inventors: Marilyn Kwolek, Danville, CA (US); Jon Block, San Francisco, CA (US)

(73) Assignee: KB Medical, LLC, Las Vegas, NV (US)

(*) Notice: Subject to any disclaimer, the term of this patent is extended or adjusted under 35 U.S.C. 154(b) by 107 days.

This patent is subject to a terminal disclaimer.

(21) Appl. No.: 16/279,907

(22) Filed: Feb. 19, 2019

(65) Prior Publication Data

US 2019/0175839 A1 Jun. 13, 2019

Related U.S. Application Data

(63) Continuation-in-part of application No. 16/035,408, filed on Jul. 13, 2018, now Pat. No. 10,881,809.
(Continued)

(51) Int. Cl.
*A61M 5/315* (2006.01)
*A61M 5/31* (2006.01)
(Continued)

(52) U.S. Cl.
CPC .......... *A61M 5/3158* (2013.01); *A61M 5/178* (2013.01); *A61M 5/3137* (2013.01);
(Continued)

(58) Field of Classification Search
CPC ............ A61M 5/3158; A61M 5/31595; A61M 5/3137; A61M 5/31515; A61M 2205/581;
(Continued)

(56) References Cited

U.S. PATENT DOCUMENTS 2,491,978 A 12/1949 Helfman et al.
2,632,445 A 3/1953 Kas et al.
(Continued)

FOREIGN PATENT DOCUMENTS

DE 202016100531 U1 2/2016
WO WO-2008083875 A1 7/2008
(Continued)

OTHER PUBLICATIONS

International Search Report and Written Opinion for PCT/US2020/018889 dated May 19, 2020.
(Continued)

*Primary Examiner* — Bhisma Mehta
*Assistant Examiner* — John J Crawford
(74) *Attorney, Agent, or Firm* — Wilson Sonsini Goodrich & Rosati

(57) ABSTRACT

A syringe exostructure includes a main body which removably receives a syringe having a syringe barrel and a syringe plunger. A drive plunger is reciprocatably mounted on the main body, and a plunger bar is slidably received in an axial channel on the drive plunger. The plunger bar is configured to removably couple to the syringe plunger when the syringe is introduced into the main body. A drive pawl assembly is fixed to an upper surface of the drive plunger and transfers forward motion of the drive plunger to the plunger bar as the drive plunger is advanced and disengages from the plunger bar when the drive plunger is retracted. A locking pawl assembly is fixed to the main body and extends through a slot formed in the bottom of the axial channel in the drive plunger. The locking pawl engages the plunger bar and allows the plunger bar to be advanced by the drive plunger as the drive plunger is advanced but prevents the plunger bar from being retracted by the drive plunger as the drive plunger is retracted.

11 Claims, 9 Drawing Sheets

Related U.S. Application Data

(60) Provisional application No. 62/548,640, filed on Aug. 22, 2017.

(51) Int. Cl.
*A61M 5/178* (2006.01)
*A61M 5/24* (2006.01)

(52) U.S. Cl.
CPC .... *A61M 5/31515* (2013.01); *A61M 5/31571* (2013.01); *A61M 5/31595* (2013.01); *A61M 5/3148* (2013.01); *A61M 5/3159* (2013.01); *A61M 2005/2414* (2013.01); *A61M 2005/3139* (2013.01); *A61M 2205/581* (2013.01); *A61M 2205/582* (2013.01)

(58) Field of Classification Search
CPC ........ A61M 2205/582; A61M 5/31565; A61M 5/31526
See application file for complete search history.

(56) References Cited

U.S. PATENT DOCUMENTS

| | | | |
|---|---|---|---|
| 2,735,431 A * | 2/1956 | Swanson | A61M 5/31595 604/223 |
| 3,110,310 A | 11/1963 | Frank et al. | |
| 4,022,207 A * | 5/1977 | Citrin | A61M 5/20 604/209 |
| 4,415,101 A | 11/1983 | Shapiro et al. | |
| 4,865,591 A | 9/1989 | Sams | |
| 5,722,956 A | 3/1998 | Sims et al. | |
| 6,699,224 B2 | 3/2004 | Kirchhofer et al. | |
| 7,699,816 B2 * | 4/2010 | Kirchhofer | A61M 5/3158 604/218 |
| 8,851,336 B2 | 10/2014 | Weill et al. | |
| 8,936,578 B2 | 1/2015 | Cronenberg | |
| 2004/0019333 A1 | 1/2004 | Graf et al. | |
| 2005/0165363 A1 * | 7/2005 | Judson | A61M 5/31551 604/209 |
| 2007/0197976 A1 | 8/2007 | Jacobs et al. | |
| 2008/0103435 A1 | 5/2008 | Graf et al. | |
| 2014/0012229 A1 | 1/2014 | Bokelman et al. | |
| 2014/0180217 A1 * | 6/2014 | Kuczek | F04B 49/14 604/208 |
| 2015/0025502 A1 | 1/2015 | Spenser et al. | |
| 2016/0213854 A1 | 7/2016 | Schwab et al. | |
| 2019/0015591 A1 * | 1/2019 | Morlok | A61M 5/326 |
| 2019/0060576 A1 | 2/2019 | Marilyn et al. | |
| 2019/0175839 A1 | 6/2019 | Kwolek et al. | |

FOREIGN PATENT DOCUMENTS

| | | |
|---|---|---|
| WO | WO-2017001923 A1 | 1/2017 |
| WO | WO-2019040228 A1 | 2/2019 |
| WO | WO-2020172323 A1 | 8/2020 |

OTHER PUBLICATIONS

International Search Report for PCTUS2018043956 dated Oct. 2, 2018.
Office action dated Apr. 13, 2020 for U.S. Appl. No. 16/035,408.
EP18848285.5 Extended European Search Report dated Apr. 8, 2021.
Notice of allowance dated Sep. 8, 2020 for U.S. Appl. No. 16/035,408.

* cited by examiner

EXOSTRUCTURE TO ASSIST IN ACCURATE SYRINGE INJECTION

CROSS-REFERENCE TO RELATED APPLICATION

The present application is a continuation-in-part of application Ser. No. 16/035,408, filed on Jul. 13, 2018, which claims the benefit of provisional application No. 62/548,640, filed on Aug. 22, 2017, the full disclosures of which are incorporated herein by reference.

BACKGROUND OF THE INVENTION

1. Field of the Invention

The present invention relates generally to the field of medical devices and methods. More specifically, the invention described herein relates to devices and methods for delivering doses of a medicament from a syringe to a patient.

Existing syringes utilize a plunger to push fluids out of a barrel through a needle and into an injection site. In the normal clinical setting, the practitioner's dominant free hand deploys the syringe with the thumb used to depress the plunger and the index and middle fingers placed on the flanges to provide direction and stabilization. Using the standard free-hand injection method, existing disposable syringes function well at delivering the total volume of the barrel as a single measured dose. However, a number of clinical interventions (e.g., botulinum toxin, deoxycholic acid, and hyaluronic acid) require that the contents of the syringe be apportioned reproducibly in separate, discrete units (i.e., doses) across multiple injection sites during the same procedure.

Free-hand injection is an inaccurate and imprecise technique for delivering discrete units at multiple sites during the same procedure with expediency. This practice carries a risk of administering an incorrect dose to an injection site, even for an experienced medical professional. The risk of administering an incorrect dose utilizing the same syringe can be due to several factors that include the change in thumb force on the plunger required to reproducibly extrude the same volume of a fluid from a syringe as well as measurement errors when attempting to visualize the barrel markings at different angles.

Therefore, a need exists for apparatus and methods for administering accurate volumetric units from a syringe filled with a medicament volume sufficient for multiple dosages.

2. Description of the Background Art

Background patents and publications include US2015025502; U.S. Pat. Nos. 4,415,101; 4,022,207; and 2,491,978.

SUMMARY OF THE INVENTION

The present invention provides a syringe exostructure intended to receive a conventional syringe and needle assembly which is either pre-filled or adapted to be filled with a medicament, such as but not limited to botulinum toxin, deoxycholic acid, and hyaluronic acid, to be delivered to a patient in multiple, sequential small aliquots or doses, usually having a volume in a range from 0.01 ml to 0.1 ml, typically from 0.025 ml to 0.05 ml. A total number of small aliquots or doses may be in the range from 10 to 100, typically from 20 to 40, and the syringe may carry a total volume of medicament in the range from 0.3 ml to 10.0 ml.

In a first aspect, the present invention comprises a syringe exostructure comprising a main body, a drive plunger, a plunger bar, a drive pawl, and a locking pawl. The main body has an upper end and a lower end, and is configured to removably receive a syringe having a syringe barrel and a syringe plunger. The syringe will typically be pre-filled with a selected medicament, and the drive plunger is reciprocatably mounted on the main body. The plunger bar is slidably mounted relative to the drive plunger and has an upper end configured to removably couple to the syringe plunger when the syringe is received on the main body. The drive pawl is disposed at a lower end of the drive plunger and is configured to engage the plunger bar to transfer downward motion to the plunger bar as the drive plunger is advanced downwardly. The drive pawl will be further configured to disengage from the plunger bar as the drive plunger is retracted upwardly. This allows the drive plunger to incrementally advance the plunger bar to deliver pre-selected doses of the medicament from the syringe, as will be described in greater detail below. The locking pawl is fixed relative to the main body and is configured to engage the plunger bar in such a way that permits the plunger bar to be advanced downwardly by the drive plunger as the drive plungers advance downwardly, but prevent the plunger bar from being retracted upwardly by the drive plunger as the drive plunger is retracted upwardly.

In specific embodiments, the plunger bar has a toothed ratchet surface which is engaged by both the drive pawl and the locking pawl. In such instances, the locking pawl is preferably formed as a living hinge coupled to the main body and oriented relative to the toothed ratchet surface to allow downward movement of the plunger bar relative to the main body while preventing upward movement of the plunger bar relative to the main body. Similarly, the drive pawl may be formed as a living hinge at a lower end of the drive plunger and will typically be oriented relative to the toothed ratchet surface so as to cause downward movement of the plunger bar relative to the main body when the drive plunger is depressed, typically by a user's thumb. The drive pawl disengages from the toothed ratchet surface as the drive plunger is raised relative to the main body (typically by a return spring), while the plunger bar is held in place by the locking pawl.

In alternate embodiments, as in more detail below, the drive pawl may comprise an assembly of a pair of pawls forming a cam mechanism pivotally attached to the drive plunger and having tips configured to engage opposed inner surfaces of a channel formed in the bottom of the plunger bar. Typically, the tip of each pawl of the drive pawl assembly comprises a toothed surface configured to engage a smooth, roughened, or toothed surface formed on the inner surfaces of the channel formed in the bottom of the plunger bar. The toothed surface on each pawl will engage the inner surfaces of the channel as the drive plunger is advanced and will disengage from the inner surfaces of the channel as the drive plunger is retracted.

In still further specific instances, the plunger bar may be slidably received in an axial channel formed on the drive plunger. The locking pawl may extend through a slot, window, or other aperture formed in the axial channel of the drive plunger, and the main body may comprise a top shell having an upper surface with a barrel groove for removably receiving the syringe barrel and a bottom shell having an upper surface which carries the locking pawl assembly. Still further, the main body may comprise a T-handle fixed to the main body with a slot or other receptacle for receiving a plunger shaft on the syringe.

In further aspects of the present invention, a method for delivering multiple doses of a medicament from a pre-filled syringe comprises attaching the pre-filled syringe to a syringe exostructure to couple a plunger button of the pre-filled syringe to a plunger bar. A drive plunger may be depressed downwardly to cause the plunger bar to advance downwardly by a pre-determined distance to, in turn, cause the plunger button to advance downwardly to dispense a pre-determined dose of the medicament from the syringe. After delivering the dose, the drive plunger will be retracted upwardly (typically by a return spring) while the plunger bar is immobilized relative to the syringe exostructure. Multiple, successive doses are delivered by repeating the second and third steps described above to deliver additional pre-determined doses of the medicament from the syringe.

In specific instances of these methods, the drive plunger may be coupled to a toothed ratchet surface on the plunger bar by a drive pawl. The plunger bar may be further immobilized by a locking pawl fixed to the syringe exostructure, where the locking pawl engages the toothed ratchet surface on the plunger bar to allow the plunger bar to advance downwardly relative to the syringe exostructure and prevent the plunger bar from moving upwardly relative to the syringe exostructure.

In further exemplary embodiments, the syringe exostructure comprises a main body configured to removably receive a syringe having a syringe barrel and a syringe plunger. A drive plunger is reciprocatably mounted on the main body, and a plunger bar is slidably received in an axial channel on the drive plunger. The drive plunger is configured to removably couple to the syringe plunger when the syringe is introduced into the main body, and a drive pawl assembly is fixed to an upper surface of the drive plunger and is configured to transfer forward motion of the drive plunger to the plunger bar as the drive plunger is advanced and is further configured to disengage from the plunger bar when the drive plunger is retracted. A locking pawl assembly is fixed to the main body and extends through a slot formed in a bottom of the axial channel in the drive plunger and configured to engage the plunger bar and allow the plunger bar to be unidirectionally advanced by the drive plunger as the drive plunger is advanced but prevents the plunger bar from being retracted by the drive plunger as the drive plunger is retracted.

In additional specific embodiments of the syringe exostructure of the present invention, the drive pawl assembly comprises a pair of pawls forming a cam mechanism pivotally attached to the drive plunger and having tips configured to engage opposed inner surfaces of a channel formed in a bottom of the plunger bar. Usually, the tip of each pawl of the drive pawl assembly comprises a toothed or other surface configured to engage and drive a mating surface, typically a smooth plastic surface, on opposed inner sides of the channel formed in the bottom of the plunger bar. Typically, the engagement surface on each pawl engages with the mating surface on the inner surfaces of the channel as the drive plunger is advanced and disengages with the surface on the inner surfaces of the channel as the drive plunger is retracted.

In further specific embodiments of the syringe exostructure of the present invention the main body comprises a top shell having an upper surface with a barrel groove for removably receiving the syringe barrel and a bottom shell having an upper surface which carries the locking pawl assembly. The main body may further comprise a hinged cover for enclosing the syringe barrel when placed in the barrel groove.

In other exemplary embodiments, a syringe exostructure constructed in accordance with the principles of the present invention may comprise a main body front having a barrel groove, a flange slot, and a plunger shroud. A plunger bar comprises a plunger button mount, a set of locking teeth, and a set of driving teeth. The plunger comprises a plunger head, a plunger spring, a set of driving pawls, a paw spring, and a fastener. A main body back comprises a locking pawl and a spring mount. The barrel groove may be enclosed by a hinged door attached to the main body front, and the plunger button mount may be moveably positioned between the flange slot and the plunger head. The plunger shroud may be positioned between the flange slot and the plunger head, and the set of driving teeth may be detachably coupled to the set of driving pawls by way of the pawl spring. The plunger spring may be elastically engaged to the spring mount opposite the plunger head, and the locking pawl may be detachably coupled to the set of locking teeth.

In further exemplary embodiments, distance between the plunger head and the plunger shroud corresponds to distance traveled by the locking pawl between each tooth of the set of locking teeth, and the syringe exostructure may still further comprise formed features surrounding the flange slot.

In further aspects of the present invention, systems may have any and/or all of the permutations and combinations of features as described previously.

BRIEF DESCRIPTION OF THE DRAWINGS

To easily identify the discussion of any particular element or act, the most significant digit or digits in a reference number refer to the figure number in which that element is first introduced.

DETAILED DESCRIPTION OF THE INVENTION

A syringe exostructure device to assist in the accurate delivery of individual units from a standard, single-use, disposable syringe filled with multiple doses. The syringe exostructure is single-use and disposable, and can be configured to support different syringe sizes and dosing requirements. The syringe exostructure includes formed features that ergonomically replicate the impression of a standard syringe. The syringe exostructure retains a syringe in place while a cam mechanism advances the syringe's plunger a set distance into the barrel to expel a measured volume with each compression of the exoskeleton plunger. Tactile and/or audible feedback(s) are provided when the plunger is compressed. The filled syringe is retained within a main body of the syringe exostructure and secured in place by the formed features and a hinged door that closes permanently and is tamper proof.

The plunger button of the syringe engages a plunger bar that advances a set distance towards the flange and the barrel when the plunger is compressed. The advancement of the plunger bar is driven by a set of driving pawls connected to the plunger that rake the plunger bar forward then disengage to return with the plunger to their starting position and reengage plunger bar closer to the plunger button. The distance traveled by the plunger head to the plunger shroud corresponds to the distance traveled by the locking pawl between each tooth of the set of locking teeth. During each advancement of the plunger bar, a locking pawl disengages the plunger bar and reengages when the plunger returns to the starting position, preventing the plunger bar from reversing direction. When the contents of the syringe have been expelled, the entire exostructure with syringe intact is discarded and cannot be reused.

A syringe exostructure in one aspect includes a main body front with a barrel groove, flange slot, and a plunger shroud; a plunger bar with a plunger button mount; a set of locking teeth; and a set of driving teeth. The plunger used with the syringe exostructure includes a plunger head, a plunger spring, a set of driving pawls, a pawl spring, and a fastener coupling: the pawl spring and the set of driving pawls to the plunger. A main body back portion of the exostructure includes a locking pawl and a spring mount.

The barrel groove is enclosably aligned to a hinged door attached to the main body front, and the plunger button is moveably positioned between the flange slot and the plunger head. The plunger shroud is positioned between the flange slot and the plunger head. The set of driving teeth is detachably coupled to the set of driving pawls by way of the pawl spring, which is elastically engaged to the spring mount opposite the plunger head. The locking pawl is detachably coupled to the set of locking teeth.

Figure 1:
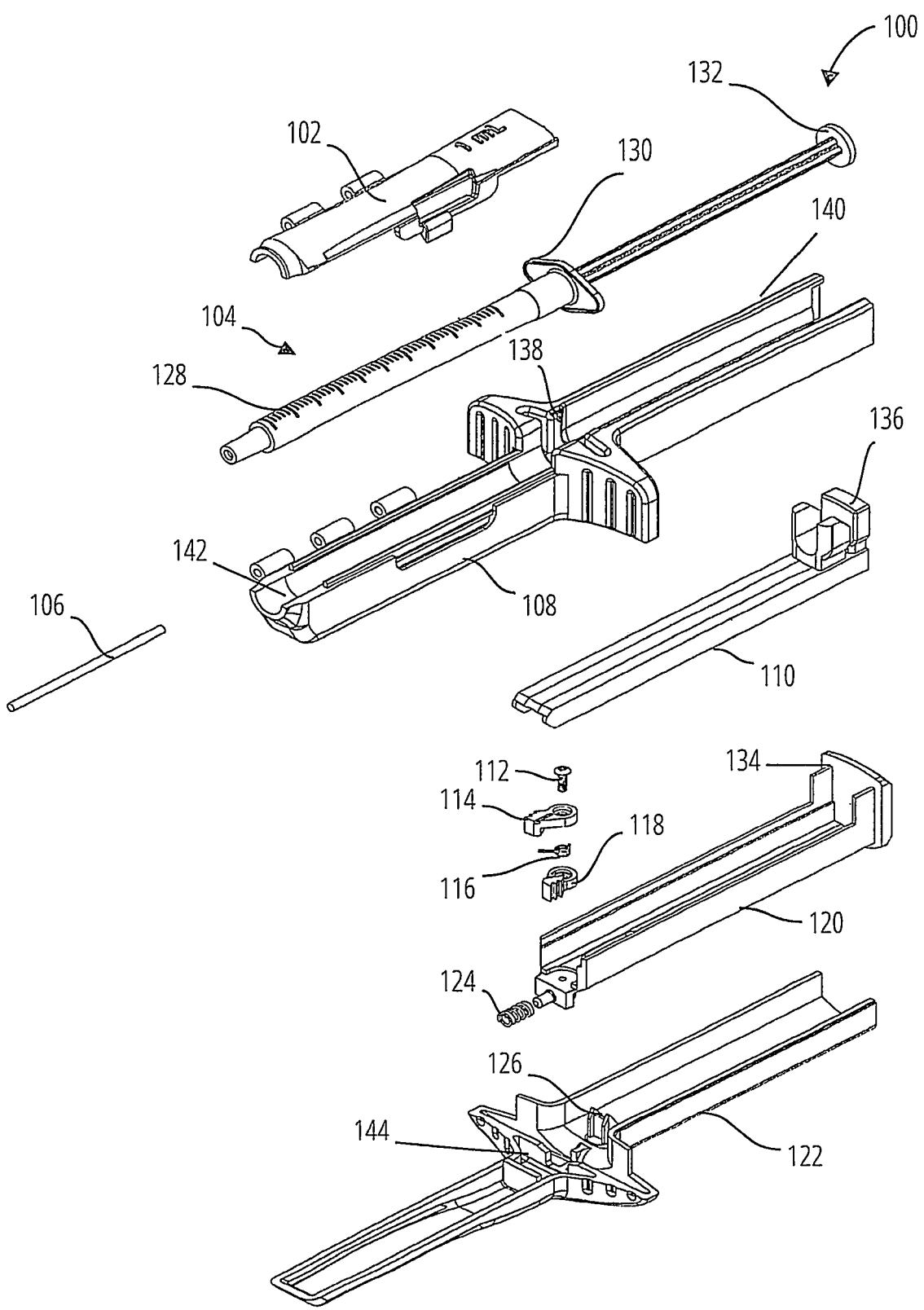
FIG. 1 illustrates a first embodiment of a syringe exostructure constructed in accordance with the principles of the present invention shown in an exploded view.

Referencing FIG. 1, a syringe exostructure 100 includes a door 102, a hinge pin 106, a main body front 108, a plunger bar 110, a fastener 112, a first driving pawl 114, a pawl spring 116, and a second driving pawl 118. A plunger 120 includes a plunger head 134, and a main body back 122 includes a locking pawl 126 and a spring mount 144. The plunger bar 110 includes a plunger button mount 136. The main body front 108 includes a barrel groove 142, flange slot 138, and a plunger shroud 140.

The syringe exostructure 100 engages a standard disposable syringe 104 that includes a barrel 128, a flange 130, and a plunger button 132. The syringe exostructure 100 delivers a highly controlled volume of fluid from a syringe 104 upon compression of the plunger 120. The main body front 108 includes a formed cavity to receive the syringe 104. The formed cavity includes structures for retaining the flange 130 and barrel 128 of the syringe 104. The flange slot 138 is surrounded by protruding structures resembling an enlarged version of the flange 130. The main body front 108 includes hinges for mounting a door 102 adjacent to the barrel of the syringe 104. The hinges of the door 102 and the main body front 108 are secured through a hinge pin 106. While secured with the hinge pin 106, the door 102 swings to enclose the barrel 128 of the syringe 104 within the formed cavity of the main body front 108.

The plunger bar 110 engages the plunger button 132 of the syringe 104. The plunger bar 110, the plunger 120, and main body back 122 are coincidently aligned along the length of the syringe 104. The plunger bar 110 is operatively coupled to the plunger 120 through a first driving pawl 114 and a second driving pawl 118, as well as to a main body back 122 through a locking pawl 126. The first driving pawl 114 and the second driving pawl 118 are mounted to the plunger 120 through a fastener 112. The first driving pawl 114 and the second driving pawl 118 elastically engage the plunger bar 110 by way of a pawl spring 116. The plunger head 134 of the plunger 120 protrudes from the main body back 122. The plunger 120 is elastically coupled to the main body back 122 through a plunger spring 124. The locking pawl 126 of the main body back 122 traverses a slotted opening through the bottom of the plunger 120 to engage the plunger bar 110 on a side opposite the syringe 104.

During operation of the syringe exostructure 100, the plunger head 134 is pushed in towards the main body back 122 until the plunger head 134 is coincident with the main body back 122. Movement of the plunger head 134 towards the main body back 122 extrudes the fluid from the barrel 128 of the syringe 104. The extrusion occurs when the first driving pawl 114 and the second driving pawl 118 move the plunger bar 110 to drive the plunger button mount 136 towards the flange 130, pushing the plunger button 132 into the barrel 128. The first driving pawl 114 and the second driving pawl 118 drive the movement of the plunger bar 110 towards the flange 130 and reposition the locking pawl 126 closer to the plunger button 132 during compression of the plunger spring 124.

When the plunger head 134 is released, the pawl spring 116 compresses, allowing the first driving pawl 114 and the second driving pawl 118 to move up the length of the plunger bar 110 towards the plunger button 132 as the plunger 120 returns to the starting position. The plunger bar 110 is kept in place relative to the movement of the plunger 120 through the engagement of the locking pawl 126. The travel distance of the plunger head 134 towards the main body back 122 is a set distance consistent with the travel distance of the locking pawl 126 along the plunger bar 110, resulting in a consistent volume extruded for each compression of the plunger head 134. The locking pawl 126 typically engages a toothed or "ratcheted" surface formed on the bottom of the plunger bar 110 to allow advancement of the plunger bar as the plunger is 120 is depressed and prevent retraction of the plunger bar as the plunger returns to its initial position. Usually, the locking pawl 126 will also provide audible and/or tactile feedback as the toothed or ratcheted bottom of plunger bar 120 is advanced by the plunger 110 over the locking pawl.

Figure 2:
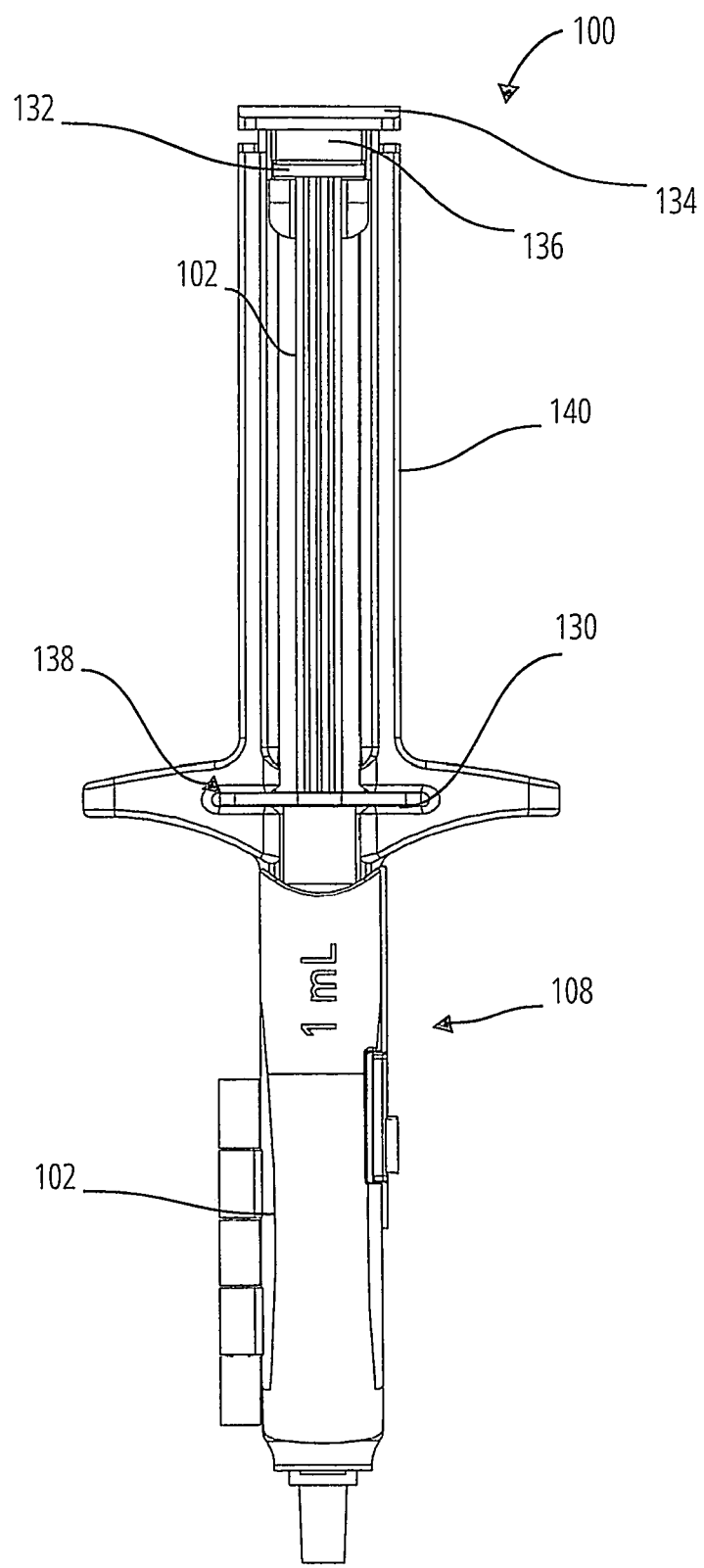
FIG. 2 illustrates a top view of the syringe exostructure of FIG. 1.

FIG. 2 illustrates a front view of an embodiment of a syringe exostructure 100, and shows the door 102, the main body front 108, the flange 130, the plunger button 132, the plunger head 134, the plunger button mount 136, the flange slot 138, and the plunger shroud 140.

Figure 3:
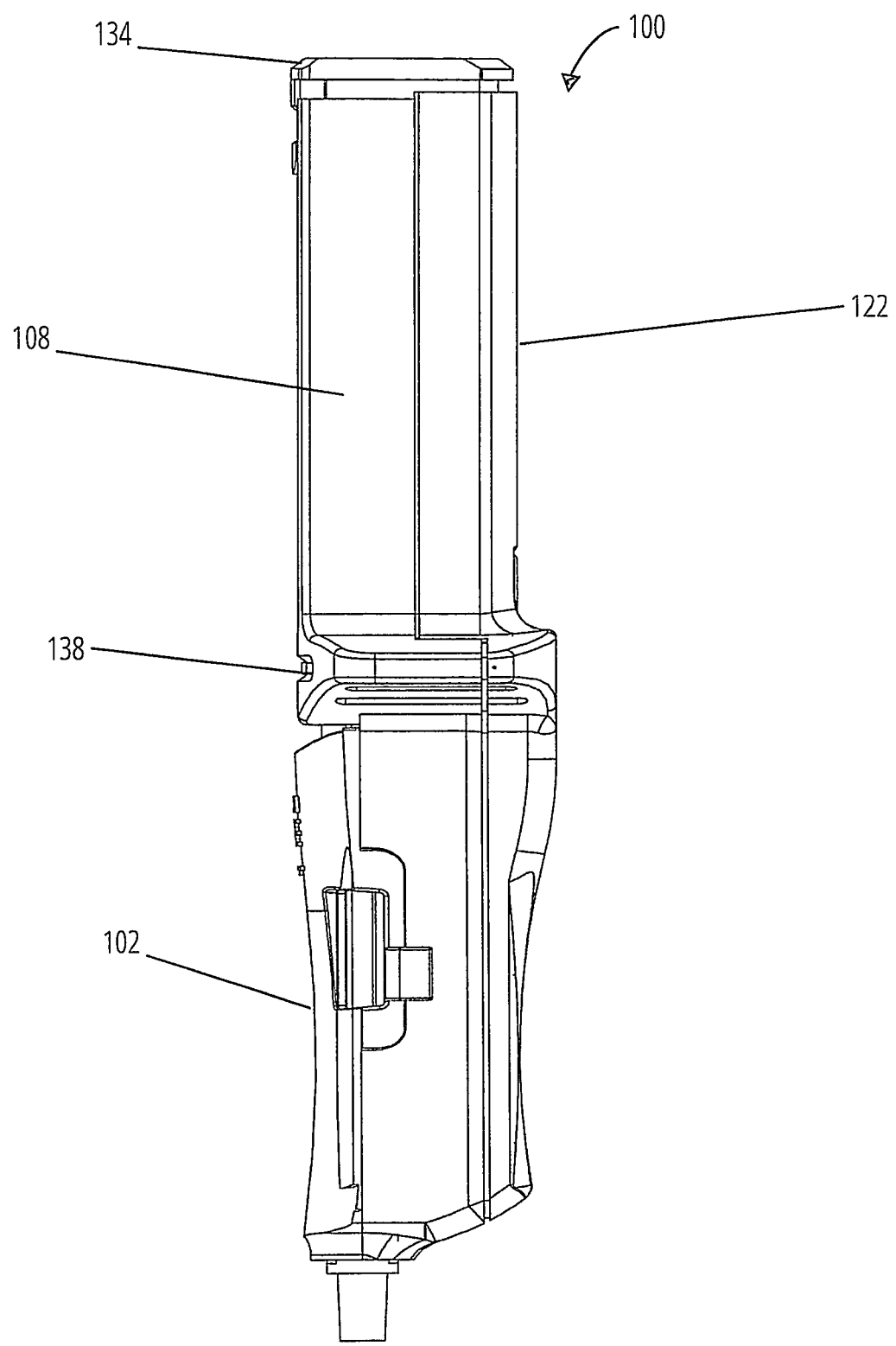
FIG. 3 illustrates a lateral view of the syringe exostructure of FIG. 1.

FIG. 3 illustrates a lateral view of the syringe exostructure 100, and shows the door 102, the main body front 108, the main body back 122; the plunger head 134, and the flange slot 138.

Figure 4:
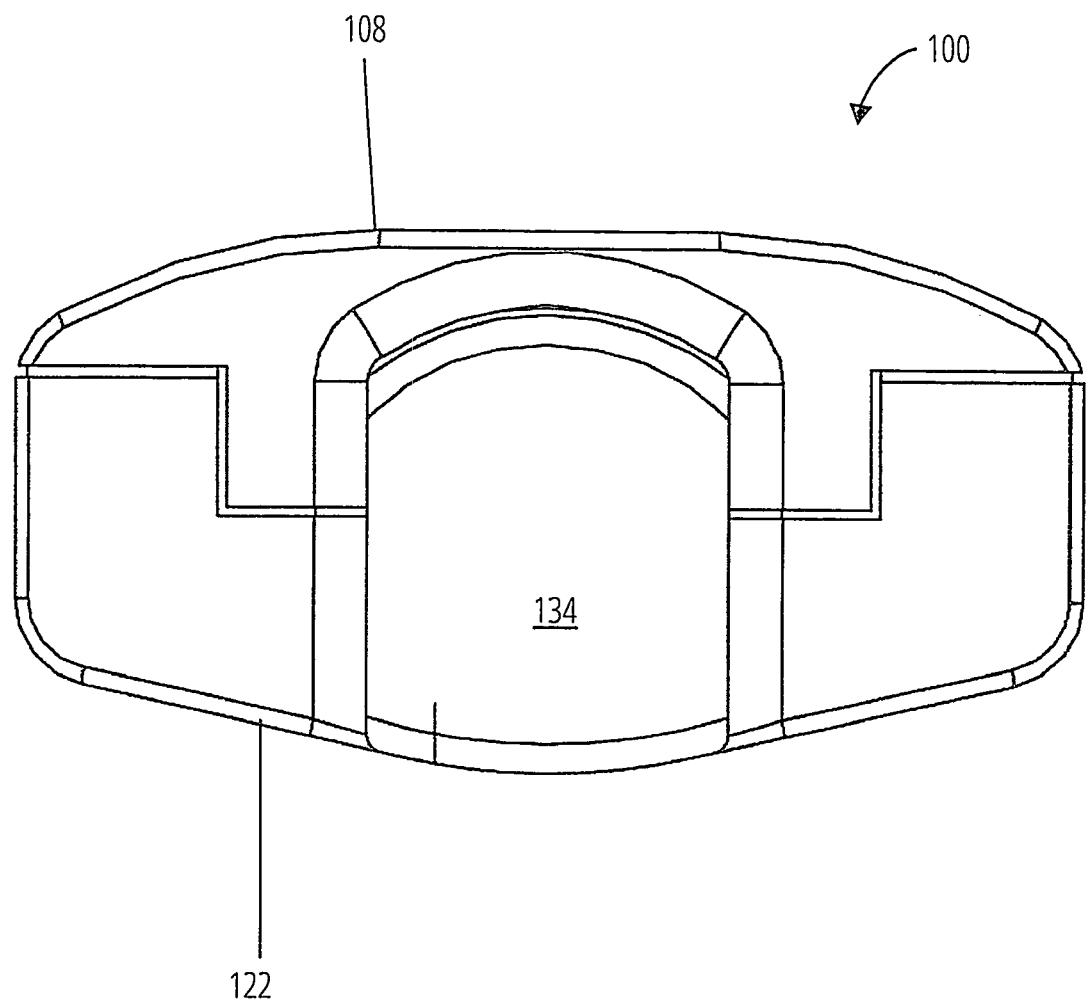
FIG. 4 is a view of a proximal or "plunger" end of the syringe exostructure of FIG. 1.

FIG. 4 illustrates a top elevational view of an embodiment of the syringe exostructure 100, showing the main body front 108, the main body back 122, and the plunger head 134.

Figure 5:
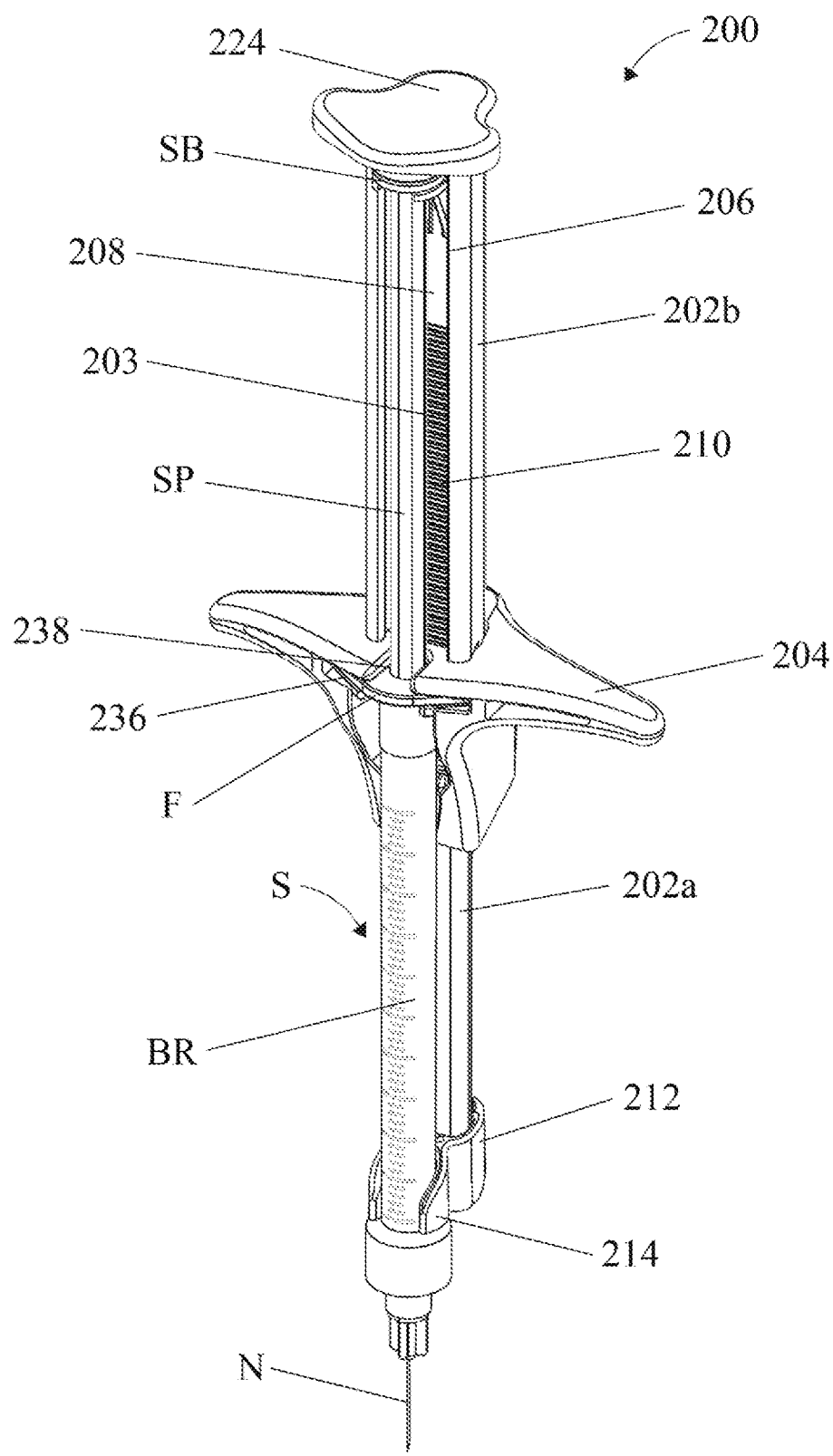
FIG. 5 is a perspective view of a second, exemplary embodiment of a syringe exostructure constructed in accordance with the principles of the present invention.
Figure 6:
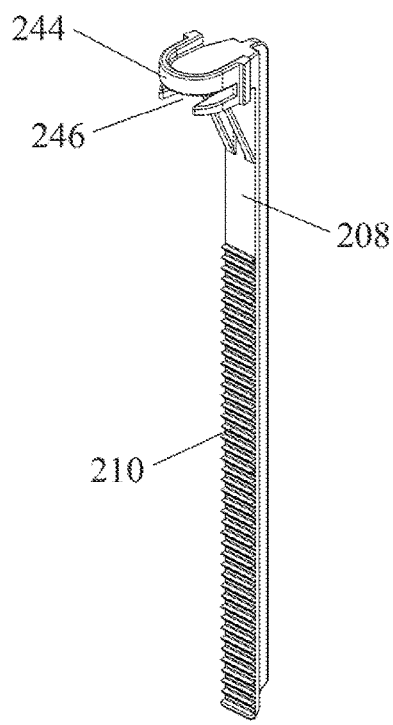
FIG. 6 illustrates an exemplary plunger bar incorporated into the embodiment of FIG. 5.

A second embodiment of the syringe exostructure of the present invention is illustrated in FIGS. 5 through 14A-14C. Referring in particular to FIGS. 5 through 11, a syringe exostructure 200 comprises a main body having a lower portion 201a and an upper portion 202b. A T-handle 204 is secured to the main body between the upper and lower portions. A drive plunger 206 and a plunger bar 208 are mounted in the upper portion of the main body 202b, typically in a channel 203, as best seen in FIG. 5.

The plunger bar 208 will typically have a plurality of ratchet teeth 210 formed on a front surface thereof. The ratchet teeth 210 allow reciprocation of the drive plunger 206 to incrementally advance the plunger bar 208, will be described in greater detail below.

Figure 13:
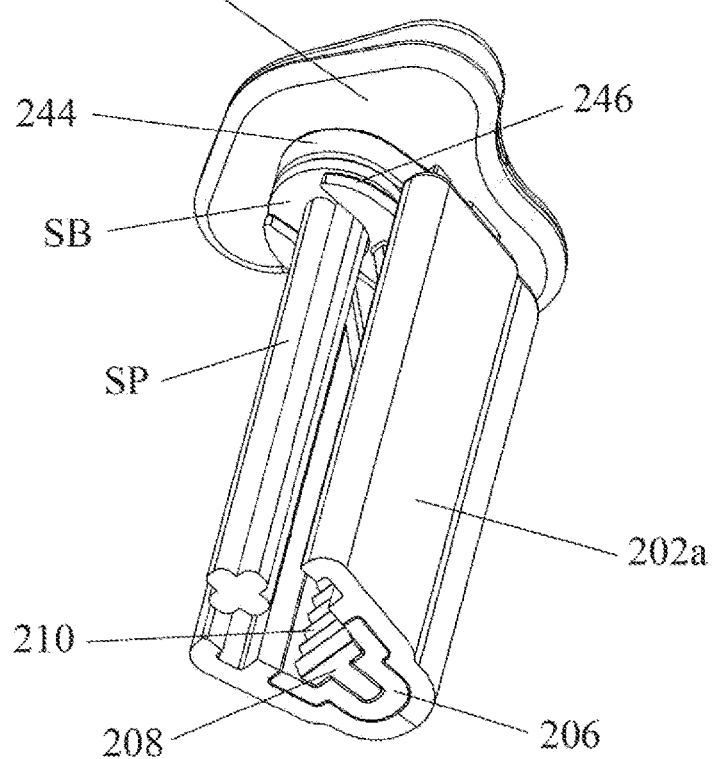
FIG. 13 is a detailed view of an upper portion of the syringe exostructure of FIG. 5 showing engagement of the plunger button of a syringe by the drive plunger.

A conventional syringe S comprises a barrel BR with a syringe plunger SP and a plunger button SB. A lower end of the syringe S above needle N is held in place by a lower cap or bracket 212 of the exoskeleton, while flanges F on a middle portion of the syringe are held in a slot 236 in the T-handle 204, and an upper end of the syringe is held by attaching the plunger button SB in a slot 246 in a button mount 244 in of the plunger bar 208 as seen in FIG. 13. The syringe plunger SP passes downwardly through a cut out 248 in the button mount 244.

Figure 7:
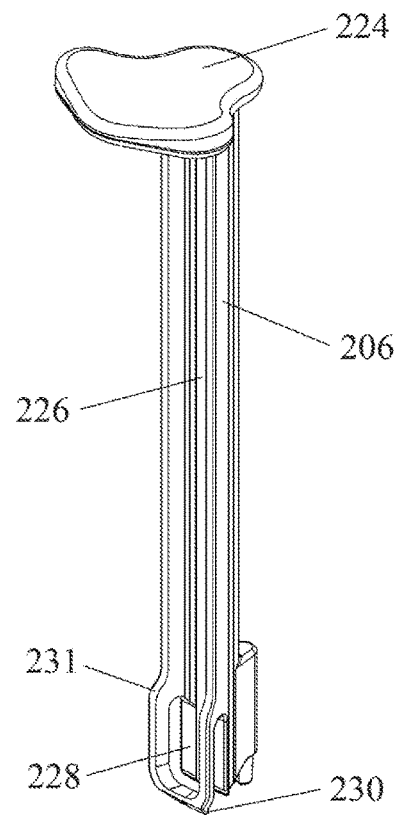
FIG. 7 illustrates an exemplary drive plunger incorporated into the embodiment of FIG. 5.
Figure 12:
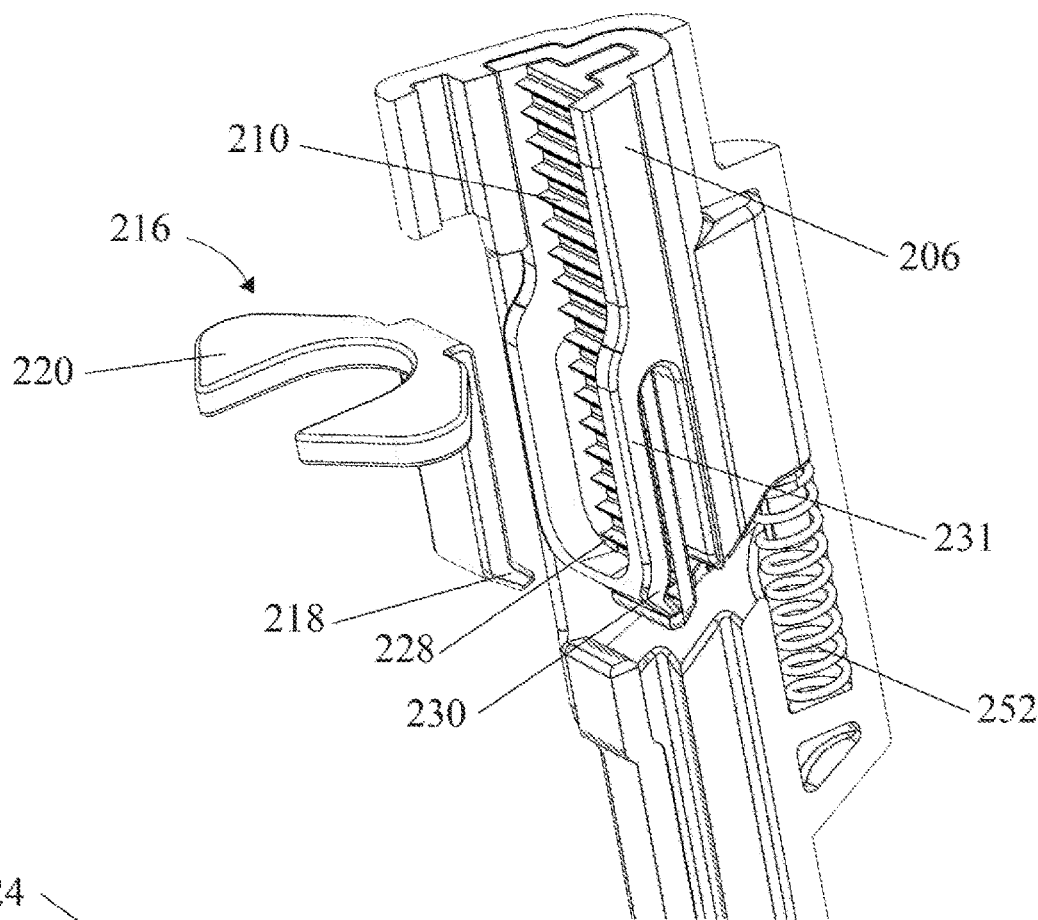
FIG. 12 is a detailed, exploded view showing details of the drive pawl and the locking pawl as they engage the plunger bar in the embodiment of FIG. 5.

Referring now to FIG. 7, the drive plunger 206 has a head 224 which is manually depressed by the user, typically using a thumb, and a channel 226 is formed in a front surface of the head for receiving the plunger bar 208, as best observed in FIGS. 12 and 13. A window 228 is formed in a lower end just of the drive plunger 206 above a drive pawl 230, where the structure of the window and drive pawl together form a living hinge 231 as also be seen in FIG. 12.

Figure 8:
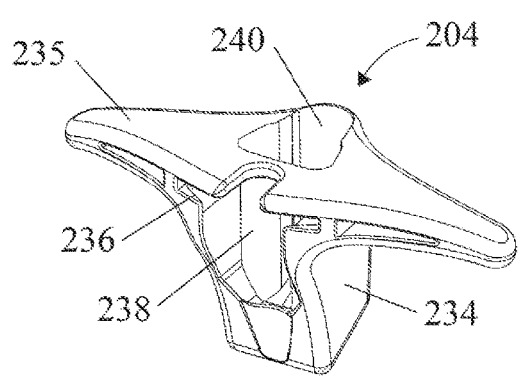
FIG. 8 illustrates an exemplary T-handle incorporated into the embodiment of FIG. 5.

Details of the T-handle 204 can be seen in FIG. 8. The T-handle includes a base 234 having a pair of lateral phalanges 235 at its upper end. The base 234 has a passage 240 which receives the main body of the syringe, as best seen in FIG. 5. A slot 236 formed in the front face of the T-handle 204 removably receives the phalange on the syringe where the syringe plunger SP passes upwardly through the groove 238.

Figures 9, 10:
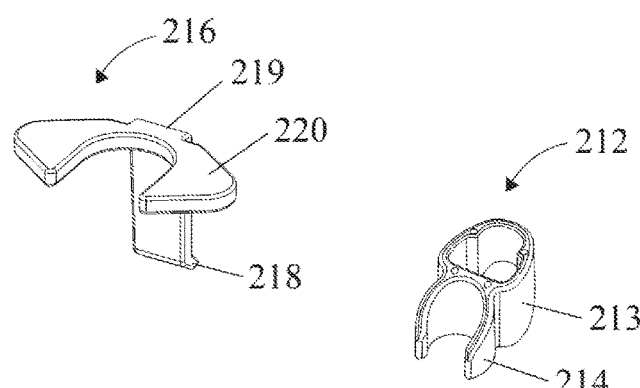
FIG. 9 illustrates an exemplary locking pawl assembly incorporated into the embodiment of FIG. 5.
FIG. 10 illustrates an exemplary lower cap or bracket incorporated into the embodiment of FIG. 5.

A locking pawl assembly 216 is illustrated in FIG. 9. The assembly includes a locking pawl 218 formed at its lower end and a yoke 220 formed at its upper end. The locking pawl 218 is attached to the yoke by a living hinge 219 which allows pivoting or flexing of the locking pawl as forces are imparted to the pawl by the ratchet teeth 210 on the plunger bar 208, as described in more detail herein below.

Referring now to FIG. 10, the lower cap or bracket 212 comprises a ring 213 which is received round the lower end of the lower portion 202a of the main body. A clasp or bracket 214 is formed on its front surface to removably receive a lower end of the syringe, as best seen in FIG. 5.

Figure 11:
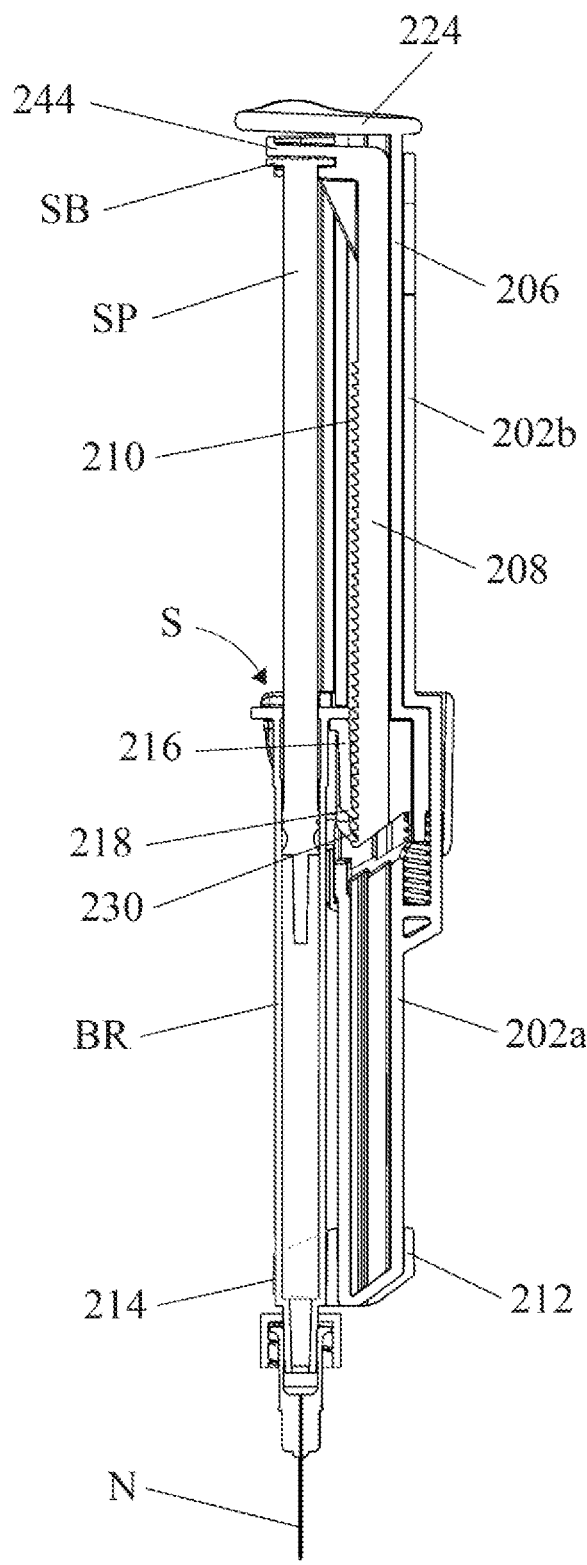
FIG. 11 is a side, sectional view of the syringe exostructure embodiment of FIG. 5.

Referring now to FIG. 11, the assembly of the syringe S in the syringe exostructure 200 is shown in partial section. In particular, it can be seen that the syringe button SB is received in the button mount 244 of the plunger bar 208 while a lower end of the toothed ratchet surface 210 of the plunger bar is engaged by the locking pawl 218 and the drive pawl 230.

Referring now to FIGS. 11 and 12, the drive pawl 230 initially engages a lower tooth of the toothed ratchet surface 210 when the syringe is unused and the syringe plunger has not been depressed. The locking pawl 218 also engages the toothed ratchet surface 210 through a window 228 formed in the drive plunger 206, and is coupled to a lower end of the drive plunger 206 by a living hinge 231, as shown in FIG. 13. A channel 203 of the upper portion 202a of the main body receives the drive plunger 206, and, in turn, the channel 226 and the drive plunger slidably receives the plunger bar 208. The syringe plunger SP is mounted so that the plunger button SB is in the slot 244.

Figure 14A:
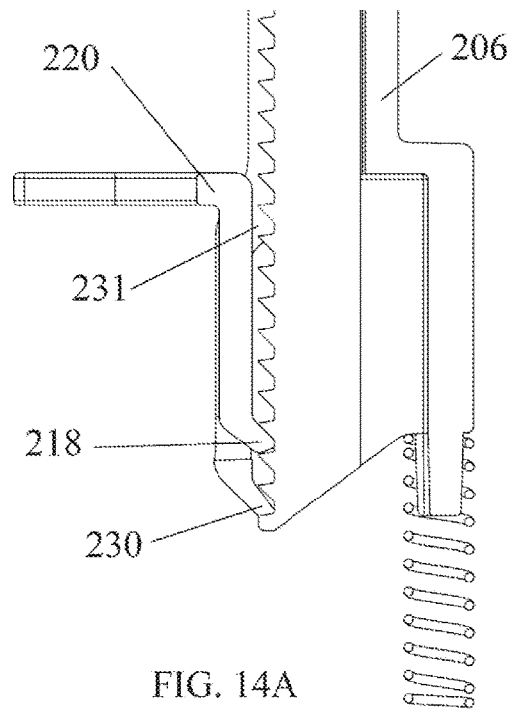
FIGS. 14A through 14C illustrate in a step-wise fashion how the drive pawl and locking pawl advance the drive plunger in accordance with the methods of the present invention.
Figure 14B:
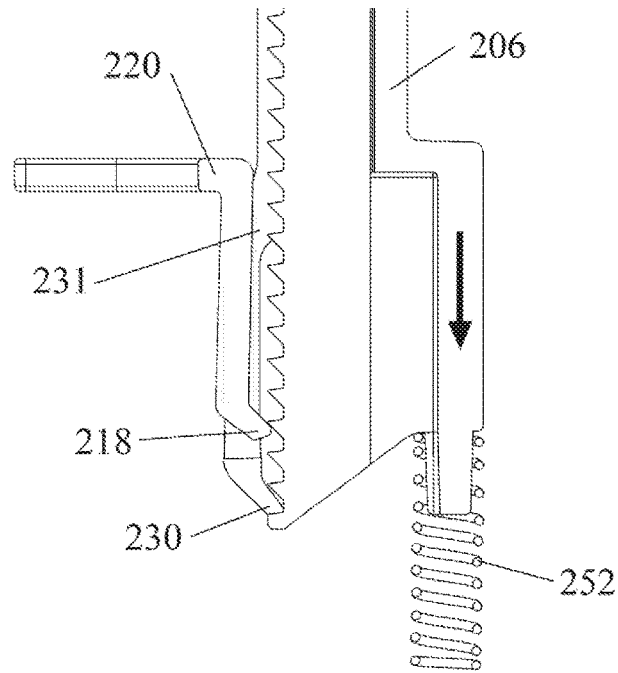
Figure 14C:
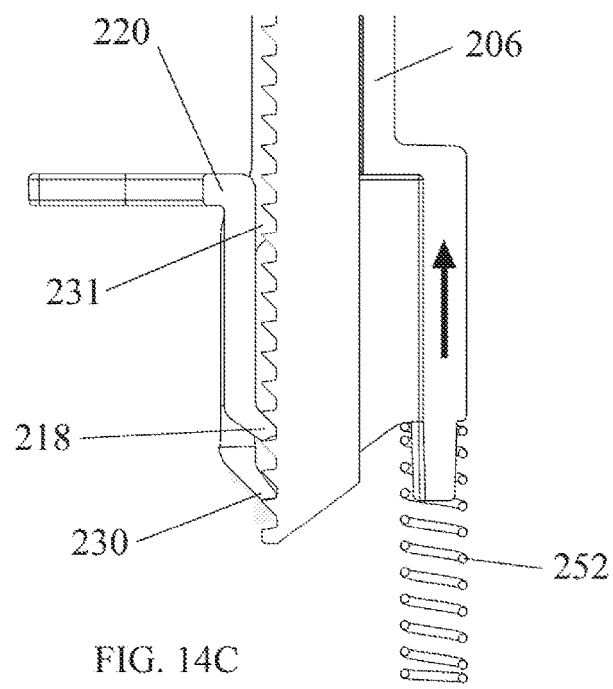

Referring now to FIGS. 14A through 14C, advancement of the syringe plunger SP by sequentially depressing the drive plunger head 224 will be describe. The drive plunger 206 and plunger bar 208 are shown in their initial configuration in FIG. 14A with the plunger bar fully extended vertically, as shown in FIGS. 5 and 11. By depressing the drive plunger head 224, the drive pawl 230 on drive plunger 206, is driven downwardly while engaging a lower tooth on the toothed ratchet surface 210 of the plunger bar 208. As the plunger bar 208 moves downwardly, the locking pawl 218 displaces rightwardly (relative to the images in FIGS. 14A-14C) and allows the adjacent tooth to pass downwardly past the locking pawl. After the drive plunger 206 has been fully depressed, the plunger bar 208 is in the configuration shown in FIG. 14, with the syringe plunger having been correspondingly depressed to dispense a dose of the medicament. After full depression of the driver plunger 206, spring 252 will cause the drive plunger to move back upwardly, as shown in FIG. 14C. Engagement of the locking pawl 218 against the adjacent tooth on the ratchet teeth surface 210 will immobilize the plunger bar 208 so that the plunger bar stays in place as the drive plunger moves upwardly back to its initial position. The drive pawl 230 will displace rightwardly as the adjacent tooth moves upwardly in a conventional ratcheting motion. As shown in FIG. 14C, the plunger bar 208 is now displaced downwardly by a notch relative to its initial position as shown in FIG. 14A. Depressing the drive plunger 206 can be repeated to sequentially depress the plunger bar 208 in order to deliver multiple doses of the medicament until the plunger bar 208 is fully extended and the medicament fully delivered from the syringe.

The foregoing examples are not intended to limit the scope of the invention. All modifications, equivalents and alternatives are within the scope of the invention.

What is claimed is:

1. A syringe exostructure comprising:
 a main body having an upper end and a lower end and being configured to removably receive a syringe having a syringe barrel and a syringe plunger;
 a drive plunger reciprocatably mounted on the main body;
 a plunger bar slidably received in an axial channel on the drive plunger and having an upper end configured to removably couple to the syringe plunger when the syringe is received on the main body;
 a drive pawl at a lower end of the drive plunger, said drive pawl configured engage the plunger bar to transfer downward motion to the plunger bar as the drive plunger is advanced downwardly and to disengage from the plunger bar as the drive plunger is retracted upwardly; and a locking pawl fixed relative to the main body and configured to engage the plunger bar and to allow the plunger bar to be advanced downwardly by the drive plunger as the drive plunger is advanced downwardly but to prevent the plunger bar from being retracted upwardly by the drive plunger as the drive plunger is retracted upwardly, wherein the locking pawl extends through a slot formed in the axial channel of the drive plunger.

2. A syringe exostructure as in claim 1, wherein the plunger bar has a toothed ratchet surface which is engaged by both the drive pawl and the locking pawl.

3. A syringe exostructure as in claim 2, wherein the locking pawl is formed as a living hinge coupled to the main body and oriented relative to the toothed ratchet surface to allow downward movement of the plunger bar relative to the main body and prevent upward movement of the plunger bar relative to the main body.

4. A syringe exostructure as in claim 3, wherein the drive pawl is formed as a living hinge at a lower end of the drive plunger and is oriented relative to the toothed ratchet surface to cause downward movement of the plunger bar relative to the main body as the drive plunger is advanced and allow upward movement of the drive plunger relative to the main body as the plunger bar is held in place by the locking pawl.

5. A syringe exostructure as in claim 1, wherein the drive pawl comprises an assembly of a pair of pawls forming a cam mechanism pivotally attached to the drive plunger and having tips configured to engage opposed inner surfaces of a channel formed in a bottom of the plunger bar.

6. A syringe exostructure as in claim 5, wherein the tip of each pawl comprises a toothed surface configured to engage a toothed surface formed on the inner surfaces of the channel formed in the bottom of the plunger bar, wherein the toothed surface on each pawl engages with the toothed surface on the inner surfaces of the channel as the drive plunger is advanced and disengages with the toothed surface on the inner surfaces of the channel as the drive plunger is retracted.

7. A syringe exostructure as in claim 1, wherein the main body comprises a top shell having an upper surface with a barrel groove for removably receiving the syringe barrel and a bottom shell having an upper surface which carries the locking pawl.

8. A syringe exostructure as in claim 7, wherein the main body further comprises a T-handle fixed to the main body with a slot for receiving a plunger shaft on the syringe.

9. A method for delivering multiple doses of a medicament from a pre-filled syringe, said method comprising:

providing a syringe exostructure as in claim 1;

(a) attaching the pre-filled syringe to the syringe exostructure to couple a plunger button of the pre-filled syringe to the plunger bar of the syringe exostructure;

(b) downwardly depressing the drive plunger on the syringe exostructure to cause the plunger bar to advance downwardly by a predetermined distance to cause the plunger button to advance downwardly to dispense a pre-determined dose of the medicament from the pre-filled syringe;

(c) retracting the drive plunger upwardly while the locking pawl immobilizes the plunger bar relative to the syringe exostructure; and (d) repeating steps (b) and (c) to deliver additional pre-determined doses of the medicament from the pre-filled syringe.

10. A method as in claim 9, wherein the drive plunger is coupled to a toothed ratchet surface on the plunger bar by the drive pawl coupled to the drive plunger.

11. A method as in claim 10, wherein the locking pawl engages the toothed ratchet surface on the plunger bar through the axial channel on the drive plunger to allow the plunger bar to advance downwardly relative to the syringe exostructure and prevent the plunger bar from moving upwardly relative to the syringe exostructure.

* * * * *